United States Patent [19]

Lee et al.

[11] Patent Number: 4,849,559

[45] Date of Patent: Jul. 18, 1989

[54] PROCESS FOR THE PREPARATION OF DICHLORO-[2,2]PARACYCLOPHANE

[75] Inventors: Chinsoo Lee; David R. Bassett, both of Charleston, W. Va.

[73] Assignee: Union Carbide Corporation, Danbury, Conn.

[21] Appl. No.: 50,016

[22] Filed: May 15, 1987

[51] Int. Cl.$^4$ .................. C07C 17/00; C07C 17/26
[52] U.S. Cl. .................. 570/199; 570/190; 570/184; 564/289; 564/282
[58] Field of Search .......... 570/184, 190, 199

[56] References Cited

FOREIGN PATENT DOCUMENTS 0220744  5/1987  European Pat. Off. .
0226225  6/1987  European Pat. Off. .
0253191  1/1988  European Pat. Off. .
807196   1/1959  United Kingdom .

*Primary Examiner*—Howard T. Mars
*Attorney, Agent, or Firm*—Jean B. Mauro

[57] ABSTRACT

A process is provided for the preparation of the dimer, dichloro-[2,2]paracyclophane, which is useful as the starting material for the deposition of conformal parylene coatings employed, for example, in the electronics industry for the protection of various sensitive electronic components.

The process avoids the normally low yields of chlorinated dimer formed by the chlorination of 2,2-paracyclophane and instead utilizes the Hofmann elimination of 2(3)-chloro-p-methylbenzyltrimethylammonium hydroxide by conducting the elimination reaction under carefully controlled conditions of reaction temperature and profile, reaction feed configuration, water concentration in the reactor and the use of a cosolvent, certain reaction promoters, or a combination thereof.

17 Claims, 2 Drawing Sheets

PROCESS FOR THE PREPARATION OF DICHLORO-[2,2]PARACYCLOPHANE

FIELD OF THE INVENTION

This invention relates in general to an improved process for the preparation of dichloro-[2,2]paracyclophane, an aromatic dimer which is used as a starting material in the preparation of parylene, an inert, transparent coating particularly useful in the electronics industry. In one aspect, this invention is directed to a process for the preparation of dichloro-[2,2]paracyclophane by the Hofmann elimination of 2(3)-chloro-p-methylbenzyltrimethylammonium hydroxide. In a further aspect, the invention relates to a process wherein the desired chlorinated paracyclophane is obtained in high yields by careful control of reaction temperature and temperature profile, reaction feed configuration, water concentration in the reactor and the use of a cosolvent and/or certain promoters or combinations thereof. The invention also relates to certain novel intermediate salts and a dichloro-[2,2]paracyclophane dimer free of undersirable chlorinated isomers.

BACKGROUND OF THE INVENTION

Parylene is a generic term applied to a class of poly-p-xylylenes which includes those derived from the chlorinated dimer of the structure:

Chlorinated di-p-xylylene, hereinafter also referred to as dichloro-[2,2]paracyclophane, upon pyrolysis followed by polymerization forms an inert, transparent, conformal coating which has excellent barrier properties and can be used at relatively high temperatures. Due to its ability to provide thin films and conform to substrates of varied geometric shapes, it is ideally suited for use as a conformal coating in a wide variety of fields, particularly in the electronics industry.

Prior to the present invention, dichloro-[2,2]paracyclophane was only prepared by the chlorination of 2,2-paracyclophane in accordance with known procedures. For example, in U.S. Pat. No. 3,221,068 which issued Nov. 30, 1965 to William F. Gorham and is assigned to Union Carbide Corporation, there is disclosed a process for halogenating 2,2-paracyclophane to form a product which can be used as the starting material in the preparation of conformal coatings.

In the process described in the Gorham patent substituted cyclic dimers were prepared by halogenating a cyclic di-p-xylylene with free chlorine or bromine to provide a dimer with as many as six halogen substituents on the aromatic rings. The process employed a Friedel-Crafts catalyst and a temperature between about 0° and 80° C. Dichloro- to hexachloro- substituted dimers are disclosed and claimed as well as the dibromo derivatives. Yields of the dichloro-di-p-xylylene as high as 99 percent are disclosed in Example 1 of the patent.

Although the process disclosed in U.S. Pat. No. 3,221,068 provides dichloro-[2,2]paracyclophane, it is not without its disadvantages. For instance, direct chlorination of 2,2-paracyclophane, results in a mixture of various amounts of chlorine atoms on the benzene rings since there are eight ring sites available in addition to the less reactive alpha sites. In practice, it has been found that the chlorination of 2,2-paracyclophane must be effected under very carefully controlled conditions if the desired dichloro derivative is to be obtained. Moreover, even with such controls, the average number of chlorine atoms per dimer molecule is slightly more than two. Hence, the product obtained is not entirely pure dichloro-[2,2]paracyclophane but contains residues of other isomers.

Additionally, while the yield of chlorinated product based on the dimer obtained by the process disclosed in the patent is high, the overall yield of dichloro-[2,2]paracyclophane, based on the p-methylbenzyltrimethylammonium salt is on average no greater than 50 percent. This is due to the fact that known processes for preparing the unsubstituted dimer itself give only low yields. Yields as low as 17–19 percent are not uncommon. Accordingly, the overall process for the application of parylene as a conformal coating is expensive and severely restricts its application to other areas where it might otherwise be used if the economics were more attractive.

More recently, U.S. Pat. No. 4,532,369, issued on July 30, 1985 to Hartmut Härtner of the Federal Republic of Germany, discloses and claims a process for the preparation of 2,2-paracyclophane from p-methylbenzyltrimethylammonium hydroxide. It is indicated in the patent that known processes which existed prior to the invention disclosed therein gave only low yields or the starting materials were not readily accessible. By contacting aqueous p-methylbenzyltrimethylammonium hydroxide with sodium or potassium hydroxide in the presence of dimethylsulfoxide (DMSO) the patentee indicated that yields as high as 70 percent were obtained. It was also indicated at column 1, lines 55–58, that the resulting high yields were surprising since the addition of other comparably aprotic solvents such as dimethylformamide, N-methyl-pyrollidone or sulfolane had no effect.

However, even though the desired 2,2-paracyclophane was obtained in good yields, it was still necessary to conduct a further, direct chlorination step, which did not avoid the problem of isomer formation.

The presence of halogenated isomers other than the desired dichloro-[2,2]paracyclophane are undesireable since it is known that alphachlorinated impurities dehalogenate under conditions employed in the deposition of parylene, causing higher than normal system pressures and possible corrosion. Moreover, conformal films prepared from chlorinated paracyclophanes, which have alpha-chlorinated impurities are inferior and lose their desirable properties more rapidly at elevated temperatures.

It was therefore desirable to find a method whereby the dichloro-[2,2]paracyclophane could be synthesized in high yield without the need for a separate chlorination step and which would avoid the formation of undesireable chlorinated isomers.

It is therefore an object of this invention to provide an improved process for the preparation of dichloro-[2,2]paracyclophane useful in the formation of parylene. Another object of the invention is to provide a process for the preparation of dichloro-[2,2]paracyclophane in which undesired isomers are absent. A still further object of this invention is to provide a process for the preparation of the chlorinated dimer in relative high yields as opposed to the methods disclosed in the literature to date. Another object of the invention is to provide a process which is simple and efficient and hence is effective in reducing the overall cost in the preparation of dichloro-[2,2]paracyclophane by circumventing the need to prepare 2,2-paracyclophane and then subjecting it to the chlorination step. It is also an object of this invention to provide a process for the preparation of dichloro[2,2]paracyclophane in high yields by means of careful control of reaction temperature and temperature profile, reaction feed configuration, water concentration in the reactor, and the use of a cosolvent and/or certain reaction promoters. Another object of this invention is to provide a process for the preparation of dichlor[2,2]paracyclophane more efficiently and in greater yields than heretofore. A still further object of the present invention is to provide certain novel intermediate salts and a dichloro-[2,2]paracyclophane which is free of undesired isomers. These and other objects will readily become apparant to those skilled in the art in the light of the teachings herein set forth.

SUMMARY OF THE INVENTION

It its broad aspect, the present invention is directed to a process for the preparation of dichloro-[2,2]paracyclophane dimer used in the preparation of parylene. The process comprises contacting an aqueous solution of 2(3)-chloro-p-methylbenzyltrimethylammonium halide with sodium or potassium hydroxide under carefully controlled conditions including reaction concentration, feed configuration, temperature profile and the use of a cosolvent and/or certain reaction promoters or a combination thereof, as hereinafter defined.

DESCRIPTION OF THE DRAWING

A more detailed understanding of the invention will be had by reference to the drawings wherein.

DETAILED DESCRIPTION OF THE INVENTION

As indicated above, the present invention provides a simple and efficient method for the preparation of the dichloro parylene dimer in relatively high yields and from readily accessible starting materials. In contrast to the teachings of the prior art which utilized chlorination of 2,2-paracyclophane, it was unexpectedly and surprisingly found that high yields of the dichloro dimer can be obtained when dichloro-[2,2]paracyclophane is prepared, not by the chlorination after formation of the 2,2-paracyclophane, but from 2(3)-chloro-p-methylbenzyltrimethylammonium halide which already contains a chlorine atom. It was also unexpectedly and surprisingly found that in order to obtain the high yields of the desired dimer it was necessary to control the reaction conditions and reactants very carefully. It was also necessary to utilize a cosolvent and/or or certain reaction promoters to optimize the reaction.

As previously indicated, the prior art methods disclosed in the literature for the preparation of dichloro-[2,2]paracyclophane involved preparation of the 2,2-paracyclophane dimer and thereafter subjecting the dimer to chlorination:

In the past, however, preparation of the dimer II by known methods resulted in low yields. Consequently, after the subsequent chlorination step. The cost of the desired product III was even further increased and the chlorinated dimer itself was a mixture of various ismomers, some of which imparted undesirable properties to the final conformal coating.

In contrast, the process of the present invention provides an efficient method for the preparation of dichloro-[2,2]paracyclophane in yields as high as 90 percent or above, and which eliminates the formation of undesireable isomers.

In general, the process of the present invention comprises the steps of:

(A) forming a mixture of:
  (a) an aqueous solution of 2(3)-chloro-p-methylbenzyltrimethylammonium halide,
  (b) an organic solvent, and
  (c) at least one member selected from the group of:
    (1) a cosolvent selected from the group consisting of DMSO and an alkyl-substituted 2-imidazolidinone,
    (2) at least one cosolvent of 1) and at least one reaction promoter, and
    (3) at least one reaction promoter,

(B) gradually adding to said mixture with stirring an aqueous solution of an alkali metal hydroxide, while maintaining the temperature below about 30° C., for a period of up to 4 hours;

(C) gradually increasing the temperature of said mixture to a temperature within the range of from about 30 to about 60° C., and maintaining the mixture at said temperature for a period of up to about 5 hours;

(D) gradually increasing the temperature of said mixture to a temperature within the range of from about 50 to about 110° C., and maintaining the mixture at said temperature for a period of time until the maximum yield of said dichloro-[2,2]paracyclophane is indicated; and (E) recovering said dichloro-[2,2]paracyclophane from said mixture.

The reaction sequence of the present invention can be shown by the following starting from the monochloro paraxylene:

As indicated by the above reaction sequence, the desired dimer is prepared by the Hofmann elimination reaction of the 2(3)-chloro-p-methylbenzyltrimethylammonium halide. During the reaction the 2(3)-chloro-p-methylbenzyltrimethylammonium hydroxide is prepared in situ by reaction of a base on the halide salt. Although the p-methylbenzyltrimethylammonium salt is known, to date it appears that there are no literature references to either the 2(3)-chloro-p-methylbenzyltrimethylammonium chloride VI or the 2(3)- chloro-p-methylbenzyltrimethylammonium hydroxide VII, and accordingly, such compounds are considered to be novel. The preparation of such compounds is set forth in Example 1.

From the above reaction, and as indicated in the examples, it is also evident that the chlorosubstituted p-methylbenzyl chloride V is prepared by chlorination of 2-chloro-paraxylene IV and reacted with trimethylamine to form the quarternary ammonium salt VI. Conversion to the intermediate hydroxide VII during the Hofmann elimination reaction, provides the desired dichloro-[2,2]paracyclophane IX which differs from III in its purity and freedom from undesirable isomers.

Thus, by the process of the present invention it is possible to prepare dichloro-[2,2]paracyclophane which is of greater purity than the product obtained by chlorination of the unsubstituted dimer.

Figure 2:
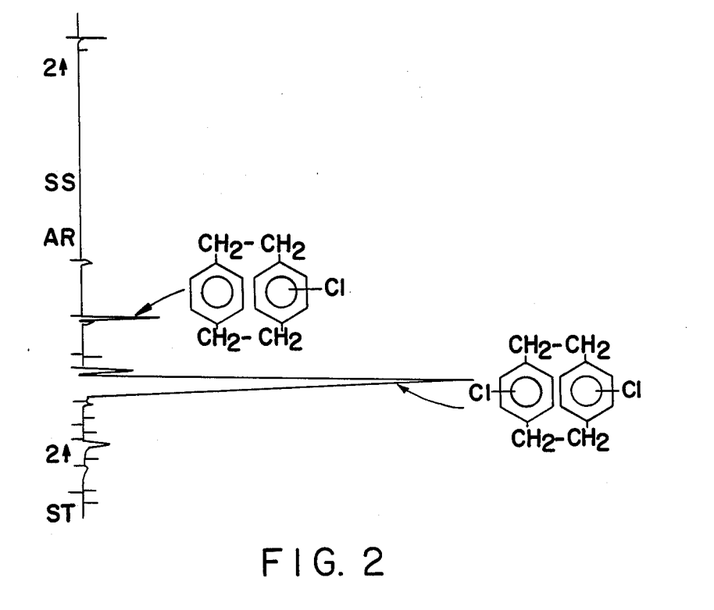
FIG. 2 is a gas chromatogram of dichloro-[2,2]paracyclophane obtained by chlorination of the 2,2-paracyclophane.
Figure 3:
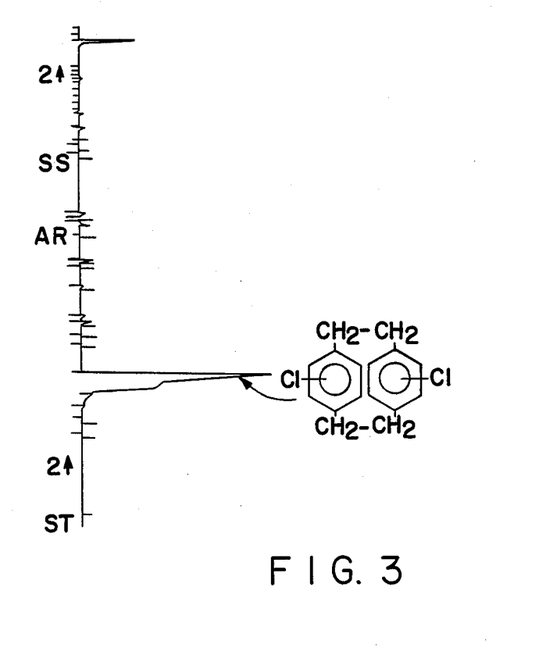
FIG. 3 is a gas chromatogram of dichloro[2,2]paracyclophane obtained in accordance with the process of the present invention.

In FIG. 3 there is shown a mass spectrogram of dichloro-[2,2]paracyclophane prepared in accordance with the process of the present invention. A chlorinated dimer free of the impurities and having the mass spectrum shown in FIG. 3 has not been reported in the literature. FIG. 2 shows a chlorinated dimer mass spectrum when the dimer was prepared by chlorination of 2,2-paracyclophane by known procedures.

As indicated above, in order to obtain high yields of the desired dichloro-[2,2]paracyclophane it is necessary to conduct the Hofmann elimination process under carefully controlled condition with particular attention to the control of reaction temperature and its profile; reaction feed configuration; water concentration in the reactor; and the use of a cosolvent or certain reaction promoters or a combination thereof.

As indicated above, the process of the present invention can be conducted in the presence of at least one cosolvent. The particular cosolvents which have been found to be ideally suited for use in the process of this invention are dimethylsulfoxide (DMSO) and an alkyl substituted 2-imidazolidinone.

The reaction promoters employed in the improved process of the present invention are those promoters which, when employed either alone or with a cosolvent, promote the Hofmann elimination reaction so as to shift the equilibrium of the reaction to favor the formation of the dimer as opposed to the competing reaction which favors polymer formation. The exact mechanism by which the reaction promoters operate is still under investigation, but it is believed that the presence of the cosolvents and/or the promoters plays a critical part in promoting the reaction to dimer formation while retarding the reaction of the dimer so formed from polymerizing to parylene.

As indicated above, the process of the present invention utilizes a cosolvent which includes dimethysulfoxide and/or an alkyl-substituted 2-imidazolidinone. Dimethylsulfoxide (DMSO) has been known as a good cosolvent for reaction intermediates in the presence of both organic and aqueous phases.

The alkyl-substituted imidazolidinone, another cosolvent for reaction intermediates, includes those having from 2 to 4 lower alkyl groups attached to the ring carbon or nitrogen atoms. Preferably the lower alkyl groups contain from 1 to 6 carbon atoms and more preferably 1 to 2 carbon atoms. The methyl-substituted imidazolidonones are the most preferred.

Illustrative compounds include 1,3-dimethyl-2-imidazolidinone, 1,3,4-trimethyl-2-imidazolidinone, 1,3,4,5-tetramethyl-2-imidazolidinone, 1,3-diethyl-2-imidazolidinone, 1,2,-dimethyl-3-ethyl-2-imidazolidinone, and the like.

It has been found that a limited number of specific reaction promoters are suitable for use in the process of the present invention, and that such promoters must be used in a specific combination if increased yields of the dimer are to be obtained.

The reaction promoters which have been found to be suitable for optimizing the yield of dimer by the process of the present invention can be classified into two different categories.

The first class of compounds which can be employed as reaction promoters in the process of the present invention are the crown ethers. These are, the cyclic ethers composed of carbon, oxygen and hydrogen. In practice, crown ethers containing from 4 to 6 oxygen atoms and from 12 to 18 carbon atoms can be employed in the process of the present invention. Particularly preferred is 18 crown 6.

Illustrative crown ethers which are suitable for use in the process of this invention are ethers such as 12 Crown 4 (1,4,7,10-tetraoxacyclododecane), 15 Crown 5 (1,4,7,10,13-pentaoxacyclopentadecane), 18 Crown 6 (1,4,7,10,13,16-hexaoxacyclooctadecane), benzo-15 Crown 5, bis[(benzo 15 Crown 5)methyl]pimelate, bis[(12 Crown 4) 2-ylmethyl]2-dodecyl-2-methyl malonate, dibenzo 18 Crown 6, dibenzo 24 Crown 6, dicyclohexano 18 Crown 6, dicyclohexano 18 Crown 6, and dicyclohexano 24 Crown 8 and the like.

The second class of reaction promoters suitable for use in the present process, are the alkoxy alkyl and the polyalkyleneoxy alkyl ethers. These compounds are sometimes referred to as "glymes" and include diglyme and tetraglyme, particularly those wherein the ether is capped with a methoxy group.

Illustrative compounds within this class include amoung others, the methyl methoxyethyl ethers of the formula:

wherein n has a value of from 1 to 18, and more preferably from 2 to 4, and m is 0 or 1 to 4.

In practice, the process of the present invention is conducted under conditions suitable for the Hofmann elimination reaction to proceed and wherein the formation of the dimer is favored over the formation of the polymerized product, i.e., parylene. It has been found that best results are obtained when the reaction is conducted in a two phase system comprised of water and an organic phase. The starting material, i.e., the 2(3)-chloro-p-methylbenzyltrimethylammonium halide is preferentially soluble in the aqueous phase whereas the dimer is preferentially soluble in the organic phase.

Any undesirable polymer formation usually occurs at the boundary between the two phases. Thus, there is always the undesirable competing reaction for polymer formation.

From the disclosure of the aforementioned Härtner patent it appeared that the yield of the 2,2-paracyclophane dimer was significantly increased when the Hofmann elimination reaction was conducted in the presence of DMSO. However, attempts to extend the teachings of the patent to conversion of 2(3)-chloro-p-methylbenzyltrimethylammonium halide to the desired chlorinated dimer in high yields were not successful as shown in Examples 3-14 and Table II. When the reaction with the appropriate 2(3)-chloro-p-methylbenzyltrimethylammonium halide was carried out in the presence of DMSO at 90° C. only about 20 percent of the desired dimer was obtained. Increasing the temperature to 110° C. caused the yield of the product to decrease to about 10 percent and a high polymer concentration was observed. Higher concentrations of DMSO did not improve the yield.

These results indicated that reaction conditions for preparing dichloro-[2,2]paracyclophane are quite different from those for preparing the unsubstituted 2,2-paracyclophane by the process disclosed in the Hartner patent. In the preparation of the 2,2-paracyclophane by the process of the patent the DMSO-quaternary salt ratio (DMSO:p-methylbenzyltrimethylammonium chloride) was important. In that reaction a variation of the reaction temperature from 90° to 125° C. did not change the yield significantly. As the temperature was increased, it was obvious that the reaction rate was increased.

After a careful study of the reaction conditions it was found that when DMSO was employed yields of the desired dichloro-[2,2]paracyclophane in the batch mode varied from 7 to 80 percent depending on the reaction conditions. It was theorized that the key variables of the reaction are not the ratio of the DMSO to quaternary salt, (DMSO:2(3)-chloro-p-methylbenzyltrimethylammonium chloride), but reaction temperature profile; reactant feed configuration; and the water concentration in the reactor.

It was noted that in order to achieve optimum yields of the desired dichlorinated dimer on a consistent basis, the mole ratio of the components in the reaction mixture should be within certain, specific ranges as indicated below:

(a) the mole ratio of alkaline hydroxide to the 2(3)-chloro-p-methylbenzyltrimethylammonium halide should be within the range of from about 2:1 to about 20:1, and preferably from about 5:1 to about 12:1.

(b) The mole ratio of the cosolvent to the quaternary salt should be within the range of from about 2:1 to about 30:1 and preferably about from about 8:1 to about 20:1.

(c) The mole ratio of water to the quaternary salt should be within the range of from about 20:1 to about 70:1 and preferably from about 40:1 to about 50:1.

(d) the mole ratio of total reaction promoters to the quarternary salt should be within the range of about 20:1 to about 10:1. In practice, it has been obvserved that when the reaction promoters is a glyme it should be present within the range of from about 4:1 to about 8:1. The mole ratio of crown ethers should be within the range of from about 3:1 to about 1:1.

(e) While the mole ratio or organic solvent to the quaternary salt is not critical, good results are obtained when the mole ratio is within the range of from about 10:1 to about 80:1 and more preferably from about 20;1 to about 60:1. It has also been noted that the amounts of cosolvent and water are interdependent, that is, if less water is employed, less cosolvent is needed.

As previously mentioned, not only are the reaction feed and water concentration important to successful operation of the process, but the temperature and temperature profile are also critical if high yields of the desired dimer are to be obtained. Thus, it has been found that by operating in a batch mode, all of the reactants, solvents and water with the exception of the hydroxide, are added to the reaction vessel and mixed at room temperature and pressure for up to about 1 to 4 hours. Thereafter, a 40-50 percent aqueous solution of the hydroxide, is added, preferably dropwise, while the temperature of the mixture is maintained so as not to exceed about 30° C.

Thereafter, after all of the hydroxide has been added, and while stirring is continued, the temperature of the reaction mixture is gradually raised to within the range of from about 30 to about 60° C., preferably from about 40 to about 45° C.

The mixture is maintain at this temperature for about 5 hours, or until such time as the reaction shows no further incremental increase in the desired product as determined by G.C. vapor-phase chromatograph. Finally the temperature of the reaction mixture is raised to within the range for from about 50 to about 110° C., preferably from about 65 to about 85° C., and maintained at this temperature for about 2 to 3 hours or until the reaction is completed as determined by gas chromatography of the sampled mixture.

Figure 1:
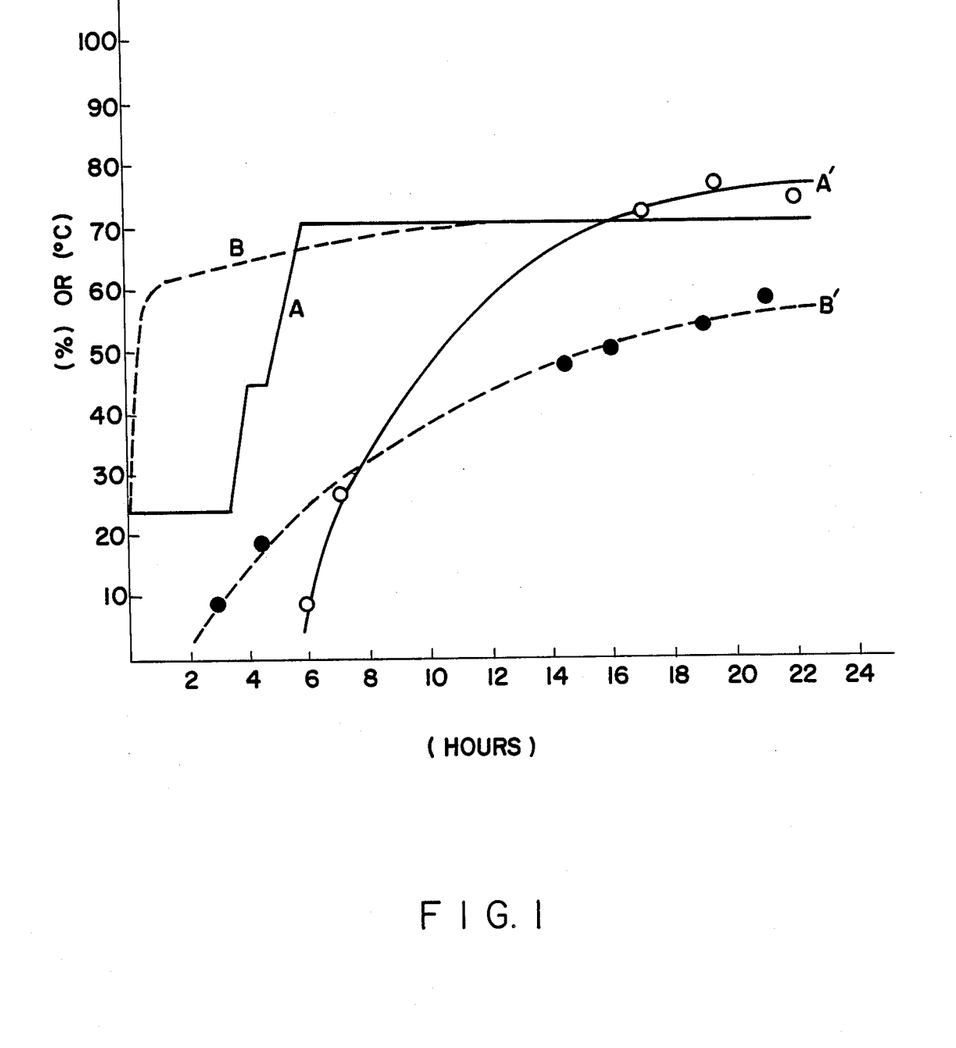
FIG. 1 is a graph showing the percent yield of the desired dimer over a period of increasing reaction time, with and without the controlled conditions of the present invention.

As is evident from FIG. 1 the dotted curve B' depicts the yield of dimer when the temperature is raised directly to about 70° C. as shown in the dotted line temperature profile B.

In contrast, however, when the temperature is increased incrementally in accordance with the above profile, as indicated by solid line A, the resulting yield, as shown by solid line A', is significantly greated than for B'.

The reaction as indicated is conducted in an aqueous phase and an organic phase. The organic phase is one in which the dimer is soluble and which the starting 2(3)-chloro-p-methylbenzyltrimethylammonium halide is largely insoluble. A wide variety of inert, water immiscible organic materials can be employed as the organic medium and include such compounds as benzene, toluene, the xylenes, such as para-yxlene, meta-xylene, ortho-xylene, hexane, octane, methylene chloride, and the like.

As indicated, the alkaline hydroxide, preferably either sodium or potassium hydroxide, is added to the reaction medium as an aqueous solution having a concentration of from about 40 to about 50 percent.

As indicated previously, it was unexpectedly and surprisingly found that by employing a cosolvent, reaction promoters and the process conditions hereinabove indicated, markedly increased yields of the dimer were obtained while polymer formation was minimized.

As previously indicated in has been noted that enhanced yields of the desired dimer can be obtained by using the cosolvent alone, or cosolvent in combination with one or more reaction promoters.

It is important that the mixture be stirred to insure intimate mixing of the organic and aqueous phases. Thereafter the phases are separated and the dimer recovered from the organic phase and purified according to known techniques.

Pressure is not critical and the reaction can be conducted at atmospheric, subatmospheric or super atmospheric pressures.

Due to the difficulties in finding an acceptable process for preparing the dimer, to date, it has been possible to achieve only minor increases in yield of the desired dimer. In many instances when high yields have been indicated in the literature, it has not been possible to reproduce them with the degree of consistency necessary for an efficient commercial operation.

As indicated above, parylene is an excellent, inert, transparent conformal coating which, due to its unusual properties, renders it particularly suitable for a wide variety of applications particularly in the electronics industry. Methods of applying the coatings starting from the dimer, and equipment for effecting such applications are all well known and readily available.

The following examples illustrate the best mode presently contemplated for the practice of this invention.

EXAMPLE 1

Preparation of Quatenary Ammonium Salt

A mixture of 2-chloro-p-xylene, azobisisobutyronitile catalyst and pyridine was charged into a reactor. While the reaction temperature was maintained at 50–60° C., chlorine was fed into the reactor over a 6 hour period. During chlorination, reactor samples were taken and analyzed for the level of 2(3)-chloro-p-methylbenzylchloride and impurities. The chlorine feed was discontinued when the level of major impurity, 2(3)-chloroalpha,alpha-dichloroparaxylene, was close to about 10 percent.

Following chlorination the amination reaction was started using 25 percent trimethylamine. The trimethylamine solution was fed at 30° C. over three hours. With addition of trimethylamine the levels of 2(3)-chloro-p-methylbenzylchloride and the major impurity were decreased in the organic phase, and were almost zero at the end of the amination reaction.

During this experiment it was observed that the aqueous phase shifted during amination. Before the trimethylamine addition the reactor showed two phases; organic phase and solid phase of pyridine.HCl. With the addition of trimethylamine solution the aqueous phase, which contains the quaternary salt, a major reaction impurity and the trimethylamine hydrochloride, moved from the top layer to the bottom layer. It was also observed that phase separation of organic/aqueous was much easier when the mixture was heated to 60° C. The quaternary salt was decanted and the organic layer recycled for the next batch. The quaternary salt concentration was estimated to be about 35.7 percent.

EXAMPLE 2

Preparation of Dichloro-[2,2]paracyclophane

A mixture of 402.5 grams of p-xylene, 12.32 grams of 2(3)-chloro-p-methylbenzyltrimethylammonium bromide in 18.48 ml of water, and 51.5 gram of DMSO and 52.5 grams of diglyme is charged and a 1 liter glass reactor equipped with stirred and condenser, Nitrogen is swept slowly through the system. The solution is maintained at 24 degree C. over 1 hour with stirring. Then a solution of 23.5 grams of KOH in 23.5 grams of water is added slowly over 2 hours with stirring at 24 degree C. The reactor temperature is raised to 45 degree C. over 1 hour period, and maintained at this temperature for 1 hour before increased to a final reactor temperature of 71 degree C. throughout the reaction study. The reactor samples are taken and measured for the dichloro-[2,2]paracyclophane concentrations in the reactor by (G.C.) vapor-phase chromatographic analysis. Product yields are also calculated based on the G.C. analysis. These values are shown in Table I below;

TABLE I

| | DICHLORO-[2,2]PARACYCLOPHANE CONCENTRATION DURING REACTION | | | | | | | | |
|---|---|---|---|---|---|---|---|---|---|
| Sample: | 1 | 2 | 3 | 4 | 5 | 6 | 7 | 8 | 9 |
| Time (hrs) | 0 | 0.5 | 2.5 | 3.8 | 5.0 | 6.3 | 16.3 | 18.55 | 22 |
| Temp. (°C.) | 24 | 24 | 24 | 45 | 71 | 71 | 71 | 71 | 71 |
| Yield | 0 | nil | nil | nil | 9.0 | 27 | 71.5 | 77.0 | 75 |

TABLE I-continued

| | DICHLORO-[2,2]PARACYCLOPHANE CONCENTRATION DURING REACTION | | | | | | | | |
|---|---|---|---|---|---|---|---|---|---|
| Sample: | 1 | 2 | 3 | 4 | 5 | 6 | 7 | 8 | 9 |
| (%) | | | | | | | | | |

EXAMPLE 3-14

COMPARATIVE PROCESS CONDITIONS

In order to demonstrate that the process conditions of the present invention are important to achieve optimum yields of the desired dimer, comparative studies were made using the same equipment and in a manner similar to that of Example 2. In the examples which are shown in Table II below, reaction temperatures and profile, molar ratio of the various components and feed configuration were varied in the presence of the cosolvents and/or reaction promoters. The yields of the desired dichloro-[2,2]paracyclophane are set forth in the second column and clearly demonstrate the wide variations which can occur if the process conditions of the present invention are not employed.

TABLE II

PREPARATION OF DICHLORO-[2,2]PARACYCLOPHANE UNDER DIFFERENT REACTION CONDITIONS

| Example | DPXC yield (%) | Reaction Temperature(°C.) | Organic Solvent | Alkaline Base | Water | DMSO | Other Cosolvent | |
|---------|----------------|---------------------------|-----------------|---------------|-------|------|-----------------|---|
| 3 | 6.8 | 90 | 41.95 p-xylene | 11.2 NaOH | 49.1 | 7.41 | — | No feed configuration. |
| 4 | 25.5 | 90–91 / 28° 110° C. 60° 25 45 1.0 | 83.7 p-xylene | 1.38 NaOH | 49.43 | 14.19 | 18crown6 0.42 | No feed configuration |
| 5 | 46.18 | (ramp profile) | 58.17 p-xylene | 9.67 KOH | 40.99 | 10.50 | Diglyme 8.23 Tetraglyme 5.06 DMI 6.905 | No feed configuration; slow increment of reaction temperature. |
| 6 | 6.0 | 106° C. / 28° →1.5← →1.5← →1.5→ | 72.95 p-xylene | 12.28 NaOH | 46.79 | 12.63 | Tetraglyme 4.42 | No feed configuration; fast increment of reaction temperature. |

TABLE II-continued
PREPARATION OF DICHLORO-[2.2]PARACYCLOPHANE UNDER DIFFERENT REACTION CONDITIONS

| Example | DPXC yield (%) | Reaction Temperature (°C.) | Organic Solvent | Alkaline Base | Water | DMSO | Other Cosolvent | |
|---|---|---|---|---|---|---|---|---|
| | | | | | Mole ratio of component to Quarternary Salt | | | |
| 7 | 17.27 | 83° C. → 24°; 1.0 ←→ 3.5 | 73.73 p-xylene | 8.71 KOH | 46.59 | 35.04 | — | No feed configuration. |
| 8 | 41.1 | 100° C.; 80° C.; 27° 0.5 ←21→ 25 ←→ 1 | 72.53 p-xylene | 6.14 NaOH | 33.13 | 12.42 | DMI 8.50 | No feed configuration |
| 9 | 1.1 | 90° C.; 1.0 FEED | 81.61 toluene | 5.16 KOH | 77.70 | 12.11 | — | The mixture of KOH, quarternary salt and water is fed to reactor. |
| 10 | 29.83 | 80° C.; 1.0 FEED | 71.61 p-xylene | 5.08 KOH | 78.68 | 12.28 | — | The mixture of KOH, quarternary salt and water is fed to reactor. |

TABLE II-continued
PREPARATION OF DICHLORO-[2.2]PARACYCLOPHANE UNDER DIFFERENT REACTION CONDITIONS

| Example | DPXC yield (%) | Reaction Temperature(°C.) | Organic Solvent | Alkaline Base | Mole ratio of component to Quarterary Salt Water | DMSO | Other Cosolvent | |
|---|---|---|---|---|---|---|---|---|
| 11 | 74.49 | 24° → 45° → 71° C., 2.0 → 4.0 KOH FEED | 72.02 p-xylene | 7.97 KOH | 44.29 | 12.52 | Diglyme 7.44 | KOH solution is fed into reactor. |
| 12 | 58.5 | 60° C. → 70° C., 2.0 KOH FEED | 73.93 p-xylene | 8.538 KOH | 46.05 | 12.62 | Diglyme 7.37 | KOH solution is fed into reactor. |
| 13 | 77.3 | 29° → 46° → 76° C., 2.0 → 3.0 KOH FEED | 40.46 p-xylene | 11.06 NaOH | 50.3 | 12.05 | DMI 22.24 | NaOH solution is fed into reactor. |
| 14 | 79.5 | 29° → 45° → 75° C., 2.0 → 3.0 → 19 NaOH FEED | 40.02 p-xylene | 11.29 NaOH | 48.41 | — | Diglyme 8.17 18crown6 0.80 | NaOH solution is fed into reactor. |

In Table II above, DPXC is the dichloro[2,2]paracyclophane; DMSO and dimethylsulfoxide; and DMI is 1,3-dimethyl-2-imidazolidinone. The numeral under the reaction temperature profiles indicates the time in hours. "No feed configuration" means that all of the components were in the reactor before heating.

As indicated in Table II, it is clearly evident that optimum yields are obtained when the process variables are carefully controlled, particularly the reaction temperature and temperature profile.

EXAMPLE 15

PREPARATION OF DICHLORO-[2,2]PARACYCLOPHANE

A mixture of 399.8 grams of p-xylene, 11.92 grams of 2(3)-chloro-p-methylbenzyltrimethylammonium bromide in 17.88 ml of water, and 50.2 grams of DMSO and 50.4 grams of diglyme is charged in a 1 liter glass reactor equipped with stirrer and condenser. Nitrogen is swept slowly through the system. The solution is maintained at 24 degree C. over 1 hour with stirring, and then the reactor temperature is raised to 63 degree C. Then a solution of 24.4 grams of KOH in 24.4 grams of water is slowly added over 2 hours with stirring 63 degree C. Reactor temperature is raised to 70 degree C. and maintained at this temperature. Stirring is continued for 30 to 40 hours at 69–71 degree C. throughout reaction study. The reactor samples are taken, and measured for the dichloro-[2,2]paracyclophane concentrations in the reactor by (G.C.) vapor-phase chromatographic analysis. Product yields are also calculated based on the G.C. analysis. The results obtained are set forth in Table III below:

TABLE III

DICHLORO-[2,2]PARACYCLOPHANE CONCENTRATION DURING REACTION

| Sample: | 1 | 2 | 3 | 4 | 5 | 6 | 7 | 8 |
|---|---|---|---|---|---|---|---|---|
| Time (hrs) | 0 | 1.3 | 2.5 | 3.8 | 13.7 | 15.5 | 18.5 | 20.5 |
| Temp. (°C.) | 24 | 63 | 63 | 66 | 71 | 70 | 70 | 71 |
| Yield (%) | 0 | nil | 9.0 | 19.0 | 48.0 | 50.5 | 53.5 | 56.5 |

EXAMPLE 16

A mixture of 314.1 grams of p-xylene, 17.4 grams of 2(3)-chloro-p-methylbenzyltrimethylammonium chloride in 31.2 ml of water, and 69.3 grams of DMSO is charged in a 1 liter glass reactor equipped with stirrer and condenser. Nitrogen is swept slowly through the system. The solution is maintained at 27 degrees C. over a period of 1 hour with stirring. Then a solution of 32.65 grams of NaOH in 32.85 grams of water is added slowly over 2 hours with stirring at 27 degrees C. The reactor temperature is raised to 45 degrees C. over 0.5 hours and maintained at this temperature for 0.5 hour before increasing to a final reactor temperature of 75 degrees C. Stirring is continued for 30–45 hours at 75 degrees C. throughout the reaction study. The reactor samples are taken, and measured for the dichloro-[2,2]paracyclophane concentrations in the reactor by (G.C.) vapor-phase chromatographic analysis. Product yields are also calculated based on the G.C. analysis. These values are shown in Table IV below:

TABLE IV

DICHLORO-[2,2]PARACYCLOPHANE CONCENTRATION DURING REACTION

| Sample: | 1 | 2 | 3 | 4 | 5 | 6 |
|---|---|---|---|---|---|---|
| Time (hrs) | 0 | 3 | 17.5 | 218 | 25.5 | 42.5 |
| Temp. (°C.) | 27 | 45 | 75 | 75 | 75 | 75 |
| Yield (%) | 0 | 3.96 | 73.7 | 76.5 | 77.7 | 77.28 |

EXAMPLE 17

A mixture of 221 grams of p-xylene, 12:17 grams of 2(3)-chloro-p-methylbenzyltrimethylammonium chloride in 21.83 ml of water, 57 grams of 1,3-dimethyl-2-imidazolidinone, and 11 grams of 18 crown 6 is charged in a 1 liter glass reactor equipped with stirrer and condenser. Nitrogen is swept slowly through the system. The solution is maintained at 29 degrees C. over a period of 1 hour with stirring. Then a solution of 23.5 grams of NaOH in 23.5 grams of water is added slowly over 2 hours with stirring at 29 degrees C. The reactor temperature is raised to 45 degrees C. over 1.5 hours and maintained at this temperature for 1.0 hour before increasing to a final reactor temperature of 75 degrees C. Stirring is continued for 20–30 hours at 75 degrees C. throughout the reaction study. The reactor samples are taken, and measured for the dichloro-[2,2]paracyclophane concentrations in the reactor by (G.C.) vapor-phase chromatographic analysis. Product yields are also calculated based on the G.C. analysis. These values are shown in Table V below;

TABLE V

DICHLORO-[2,2]PARACYCLOPHANE CONCENTRATION DURING REACTION

| Sample: | 1 | 2 | 3 | 4 | 5 | 6 | 7 | 8 |
|---|---|---|---|---|---|---|---|---|
| Time (hrs) | 0 | 5.25 | 10.3 | 14.3 | 18.3 | 20.3 | 22.3 | 24.3 |
| Temp. (°C.) | 29 | 45 | 55 | 65 | 69 | 69 | 73 | 75 |
| Yield (%) | 0 | nil | 28.6 | 50.2 | 70.3 | 74.9 | 78.8 | 79.5 |

EXAMPLE 18

PREPARATION OF DICHLOR-[2,2] PARACYCLOPHANE

A mixture of 314 grams of p-xylene, 17.28 grams of 2(3)-chloro-p-methylbenzyltrimethylammonium chloride in 35.32 ml of water, and 69.5 grams of DMSO is charged in a 1 liter glass reactor equipped with stirrer and condenser. Nitrogen is swept slowly through the system. The solution is maintained at 27 degree C. over 1 hour with stirring. Then a solution of 32.65 grams of NaOH in 32.65 grams of water is slowly added over 2 hours with stirring at 27 degree C. Reactor temperature is raised to 45 degree C. over 0.5 hour period and maintained at this temperature before raising to a final reactor temperature at 75 degree C. Stirring is continued for 25 to 30 hours at 69–71 degree C. throughout reaction study. The reactor samples are taken, and measured for the dichloro-[2,2]paracyclophane concentrations in the reactor by (G.C.) vapor-phase chromatographic analysis. Product yields are also calculated based on the G.C. analysis. The results obtained are set forth in Table VI below:

TABLE VI

| DICHLORO-[2,2]PARACYCLOPHANE CONCENTRATION DURING REACTION | | | | | | |
|---|---|---|---|---|---|---|
| Sample: | 1 | 2 | 3 | 4 | 5 | 6 |
| Time (hrs) | 0 | 2.5 | 5.0 | 7.0 | 23.5 | 27 |
| Temp. (°C.) | 27 | 46 | 75 | 75 | 75 | 75 |
| Yield (%) | 0 | — | 73 | 89 | 95 | 92 |

EXAMPLE 19

PREPARATION OF DICHLORO-[2,2]PARACYCLOPHANE

A mixture of 401 grams of p-xylene, 40.5 grams of NaOH in 40.5 ml of water, 24.08 grams of 2(3)-chloro-p-methylbenzyltrimethylammonium bromide in 24.08 ml of water, and 52.1 grams of DMSO is charge to a 1 liter glass reactor equipped with stirrer and condenser. Nitrogen is swept slowly through the system. The solution is heated to 90 degree C. over 1 hour with stirring. Stirring is continued for hours at 90–91 degree C. throughout reaction study. The reactor samples are taken, and measured for the dichloro-[2,2]paracyclophane concentrations in the reactor by (G.C.) vapor-phase chromatographic analysis. Product yields are also calculated based on the G.C. analysis. The results obtained are set forth in Table VII below:

TABLE VII

| DICHLORO-[2,2]PARACYCLOPHANE CONCENTRATION DURING REACTION | | | | | |
|---|---|---|---|---|---|
| Sample: | 1 | 2 | 3 | 4 | 5 |
| Time (hrs) | 0 | 1.0 | 2.7 | 3.7 | 5.7 |
| Temp. (°C.) | 24 | 90 | 90 | 90 | 90 |
| Yield (%) | 0 | nil | 2.7 | 6.9 | 6.8 |

It is readily apparent from the above data that it is important to utilize specific conditions in order to obtain the maximum yields of the desired chlorinated dimer.

The present invention accordingly provides a unique and efficient process for the preparation of the desired dimer in high yields and of an exceptional degree of purity compared to that previously obtainable by the prior art methods. The process of this invention accordingly has the advantage over known methods by a) increasing the yield of desired dimer b) eliminating a chlorination step, and c) providing a dimer which is free of undesirable isomers which have detrimental effects on the resulting conformal coating prepared therefrom.

Although the invention has been illustrated by the preceding examples, it is not to be construed as being limited to the materials employed therein, but rather the invention is directed to the generic area as hereinbefore disclosed. Various modifications and embodiments thereof may be made without departing from the spirit or scope thereof.

What is claimed is:

1. A process for the preparation of dichloro-[2,2]paracyclophane used in the preparation of parylene, which comprises the steps of:
    (A) forming a mixture of:
        (a) an aqueous solution of 2(3)-chloro-p-methylbenzyltrimethylammonium halide,
        (b) an organic solvent, and
        (c) at least one member selected from the group consisting of:
            (1) a cosolvent selected from the group consisting of DMSO and an alkyl sub-stituted 2-imidazolidinone,
            (2) at least one cosolvent of (1) and at least one reaction promoter, and
            (3) at least one reaction promoter selected from the group consisting of:
                (a) crown ethers, and
                (b) glymes,
    (B) gradually adding to said mixture with stirring an aqueous solution of an alkali metal hydroxide, while maintaining the temperature below about 30° C., for a period of up to 4 hours;
    (C) gradually increasing the temperature of said mixture to a temperature within the range of from about 30° to about 60° C., and maintaining the mixture at said temperature for a period of up to about 5 hours;
    (D) gradually increasing the temperature of said mixture to a temperature within the range of from about 50° to about 110° C., and maintaining the mixture at said temperature for a period of time until the maximum yield of said dichloro-[2,2]paracyclophane is indicated; and
    (E) recovering said dichloro-[2,2]paracyclophane from said mixture.

2. The process of claim 1 wherein the process is effected in the presence of an inert water-immiscible organic solvent.

3. The process of claim 2 wherein said solvent is selected from the group of toluene, benzene, the xylenes, hexane, octane and methylene chloride.

4. The process of claim 1 wherein said cosolvent is dimethylsulfoxide.

5. The process of claim 1 wherein said cosolvent is 1,3-dimethyl-2-imidazolidinone.

6. The process of claim 1 wherein said cosolvent is employed in combination with a glyme.

7. The process of claim 6 wherein said cosolvent is employed in combination with a glyme and a crown ether.

8. The process of claim 6 wherein said cosolvent is dimethysulfoxide.

9. The process of claim 6 wherein said cosolvent is an alkyl-substituted imidazolidinone 10. The process of claim 1 wherein said cosolvent is a combination of dimethylsulfoxide and an alkyl-substituted 2-imidazoldinone.

11. The process of claim 10 wherein said 2-imidazolidinone cosolvent is 1,3-dimethyl-2-imidazolidinone.

12. The process of claim 1 wherein said crown ether is 1,4,7,10,13,16-hexaoxacyclooctadecane.

13. The process of claim 1 wherein said reaction promoter is diglyme.

14. The process of claim 1 wherein said reaction promoter is tetraglyme.

15. The process of claim 1 wherein said hydroxide is sodium hydroxide.

16. The process of claim 1 wherein said hydroxide is potassium hydroxide.

17. A process for the preparation of dichloro-[2,2]paracyclophane used in the preparation of parylene, which comprises the steps of:
(A) forming a mixture of:
  (a) an aqueous solution of 2(3)-chloro-p-methyl-benzyltrimethylammonium chloride,
  (b) an organic solvent, and
  (c) at least one member selected from the group consisting of:
    (1) a cosolvent selected from the group consisting of dimethylsulfoxide and 1,3-dimethyl-2-imidazol idinone,
    (2) at least one cosolvent of (1) and at least one reaction promoter, and
    (3) at least one reaction promoter selected from the group consisting of:
      (a) crown ethers, and
      (b) glymes,
  the mole ratio of said cosolvent to said chloride being within the range of from about 2:1 to about 30:1;
  the mole ratio of said organic solvent to said chloride being within the range of from about 10:1 to about 80:1,
  and the mole ratio of water to said chloride being with the range of from about 20:1 to about 70:1,
(B) gradually adding to said mixture with stirring an aqueous solution of an alkali metal hydroxide, while maintaining the temperature below about 30° C. for a period of up to 4 hours;
(C) gradually increasing the temperature of said mixture to a temperature within the range of from about 30° to about 60° C., and maintaining the mixture at said temperature for a period of up to about 5 hours;
(D) gradually increasing the temperature of said mixture to a temperature within the range of from about 50° to about 110° C., and maintaining the mixture at said temperature for a period of time until the maximum yield of said dichloro-[2,2]paracyclophane is indicated; and
(E) recovering said dichloro-[2,2]paracyclophane from said mixture.

* * * * *